(12) United States Patent
Ortwine et al.

(10) Patent No.: US 6,297,247 B1
(45) Date of Patent: *Oct. 2, 2001

(54) SULFONAMIDE INHIBITORS OF MATRIX METALLOPROTEINASES

(75) Inventors: Daniel F. Ortwine, Saline; Claude F. Purchase, Jr., Ann Arbor; Andrew D. White, Lakeland, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/599,306

(22) Filed: Jun. 22, 2000

Related U.S. Application Data

(62) Division of application No. 09/412,707, filed on Oct. 5, 1999, now Pat. No. 6,153,612, which is a division of application No. 09/068,726, filed as application No. PCT/US96/16761 on Oct. 18, 1996.
(60) Provisional application No. 60/007,372, filed on Nov. 17, 1995.

(51) Int. Cl.[7] ............... A61K 31/451; A61K 31/495
(52) U.S. Cl. ............... 514/255.03; 514/252.12; 514/252.13; 514/254.09; 514/323; 514/326; 514/331
(58) Field of Search .............. 514/252.12, 252.13, 514/255.03, 326, 331, 254.09, 323

(56) References Cited

U.S. PATENT DOCUMENTS

| | | | |
|---|---|---|---|
| 5,455,258 | 10/1995 | MacPherson et al. | 514/357 |
| 5,506,242 | 4/1996 | MacPherson et al. | 514/336 |
| 5,514,716 | 5/1996 | Gowravaram et al. | 514/563 |
| 5,552,419 | 9/1996 | MacPherson et al. | 514/357 |
| 5,618,844 | 4/1997 | Gowravaram et al. | 514/575 |
| 5,672,615 | 9/1997 | MacPherson et al. | 514/357 |
| 5,747,514 | 5/1998 | Beckett et al. | 514/352 |
| 5,817,822 | 10/1998 | Nantermet et al. | 546/194 |
| 5,859,253 | 1/1999 | Beckett et al. | 546/306 |
| 5,919,940 | 6/1999 | Martin | 548/195 |
| 5,948,780 | * 9/1999 | Peterson et al. | 514/255 |

* cited by examiner

Primary Examiner—Richard L. Raymond
(74) Attorney, Agent, or Firm—Charles W. Ashbrook

(57) ABSTRACT

Sulfonamide compounds are described which are inhibitors of matrix metalloproteinases, particularly stromelysin-1 and gelatinase A (72 kD gelatinase). Also described are methods for the treatment of multiple sclerosis, atherosclerotic plaque rupture, aortic aneurism, heart failure, restenosis, periodontal disease, corneal ulceration, burns, decubital ulcers, chronic ulcers or wounds, cancer metastasis, tumor angiogenesis, arthritis, or other autoimmune or inflammatory disorders dependent upon tissue invasion by leukocytes using the compounds.

15 Claims, No Drawings

SULFONAMIDE INHIBITORS OF MATRIX METALLOPROTEINASES

This is a division of U.S. Ser. No. 09/412,707, Oct. 5, 1999 now U.S. Pat. No. 6,153,612, which is a division of U.S. Ser. No. 09/068,726, now U.S. Pat. No. 5,977,141, which is a 371 of PCT/US96/16761 filed Oct. 18, 1996, which claims priority from Provisional Application No. 60/007,372 filed Nov. 17, 1995.

FIELD OF THE INVENTION

The present invention relates to sulfonamide compounds that inhibit matrix metalloproteinases, pharmaceutical compositions that include these compounds, and pharmaceutical methods of treatment using these compounds.

BACKGROUND OF THE INVENTION

The novel compounds of the present invention are inhibitors of matrix metalloproteinases, e.g., stromelysin-1 and gelatinase A (72 kDa gelatinase). More particularly, the compounds of the present invention are useful in the treatment of atherosclerotic plaque rupture, aortic aneurism, heart failure, restenosis, periodontal disease, corneal ulceration, burns, decubital ulcers, chronic ulcers or wounds, cancer metastasis, tumor angiogenesis, arthritis, multiple sclerosis, and other autoimmune or inflammatory disorders dependent on the tissue invasion of leukocytes or other activated migrating cells.

Stromelysin-1 and gelatinase A are members of the matrix metalloproteinase (MMP) family (Woessner J. F., *FASEB J.* 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C., *J. Biol. Chem.*, 1994; 269:16766–16773), and the newly discovered membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is the focal point for inhibitor design. The modification of substrates by introducing chelating groups has generated potent inhibitors such as peptide hydroxamates and thiol-containing peptides. Peptide hydroxamates and the natural endogenous inhibitors of MMPs (TIMPS) have been used successfully to treat animal models of cancer and inflammation.

The ability of the matrix metalloproteinases to degrade various components of connective tissue makes them potential targets for controlling pathological processes. For example, the rupture of atherosclerotic plaques is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galla Z. S., Sukhova G. K., Lark M. W., and Libby P., "Increased expression of matrix metalloproteinases and matrix degrading activity in vulnerable regions of human atherosclerotic plaques", *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l. Acad. Sci.,* 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases", *Clin. Sci.,* 1991;81:233–239).

Heart failure arises from a variety of diverse etiologies, but a common characteristic is cardiac dilation which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy", *Clin. Res.,* 1993;41:660A; Tyagi S. C., Reddy H. K., Voelker D., Tjara I. E., and Weber K. T., "Myocardial collagenase in failing human heart", *Clin. Res.,* 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction", *Can. J. Cardiol.,* 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure", *Am. J. Physiol.,* 1992;263:H266–H270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat", *Circulation Research,* 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSCMs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation", *Circulation Research,* 1994;75:41–54).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva", *J. Periodontal Res.,* 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva", *J. Periodontal Res.,* 1987;22:81–88). Proteolytic degradation of extracellular matrix has been observed in corneal ulceration following alkali burns (Brown S. I., Weller C. A., and Wasserman H. E., "Collagenolytic activity of alkali burned corneas", *Arch. Opthalmol.,* 1969;81:370–373). Thiol-containing peptides inhibit the collagenase isolated from alkali-burned rabbit corneas (Burns F. R., Stack M. S., Gray R. D., and Paterson C. A., *Invest. Opththamol.,* 1989;30:1569–1575).

Stromelysin is produced by basal keratinocytes in a variety of chronic ulcers (Saarialho-Kere U. K., Ulpu K., Pentland A. P., Birkedal-Hansen H., Parks W. C., Welgus H. G., "Distinct populations of basal keratinocytes express stromelysin-1 and stromelysin-2 in chronic wounds", *J. Clin. Invest.,* 1994;94:79–88).

Stromelysin-1 mRNA and protein were detected in basal keratinocytes adjacent to but distal from the wound edge in what probably represents the sites of proliferating epidermis. Stromelysin-1 may thus prevent the epidermis from healing.

Davies, et al., (*Cancer Res.,* 1993;53:2087–2091) reported that a peptide hydroxamate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., Cancer Res., 1992;52:2353–2356), and the natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.,* 1992;52:701–708). Studies of human cancers have shown that gelatinase A is activated on the invasive tumor cell surface (Strongin A. Y., Marmer B. L., Grant G. A., and Goldberg G. I., *J. Biol Chem.,* 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., *Cancer Res.,* 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute,* 1995;87:293; and Benelli R., Adatia R., Ensoli B., Stetler-Stevenson W. G., Santi L., and Albini A., *Oncology Research,* 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury", *Arthritis Rheum.,* 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia", *J. Rheumatol.,* 1993;20:693–697). TIMP-1 and TIMP-2 prevented the formation of collagen fragments, but not proteoglycan fragments, from the degradation of both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions,* 1992;37:147–154; Ellis A. J., Curry V. A., Powell E. K., and Cawston T. E., *Biochem. Biophys. Res. Commun.,* 1994;201:94–101).

Gijbels, et al., (J. Clin. Invest., 1994;94:2177–2182) recently described a peptide hydroxamate, GM6001, that suppressed the development or reversed the clinical expression of experimental allergic encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M. and Madri J. A., "The Induction of 72-kD Gelatinase in T Cells upon Adhesion to Endothelial Cells is VCAM-1 Dependent", *J. Cell Biology,* 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provided the basis for the belief that an inhibitor of stromelysin-1 and/or gelatinase A will treat diseases involving disruption of extracellular matrix resulting in inflammation due to lymphocytic infiltration, inappropriate migration of metastatic or activated cells, or loss of structural integrity necessary for organ function.

We have identified a series of sulfonamide compounds that are inhibitors of matrix metalloproteinases, particularly stromelysin-1 and gelatinase A, and thus useful as agents for the treatment of multiple sclerosis, atherosclerotic plaque rupture, restenosis, aortic aneurism, heart failure, periodontal disease, corneal ulceration, burns, decubital ulcers, chronic ulcers or wounds, cancer metastasis, tumor angiogenesis, arthritis, or other autoimmune or inflammatory diseases dependent upon tissue invasion by leukocytes.

SUMMARY OF THE INVENTION

The present invention provides compounds of the Formula I

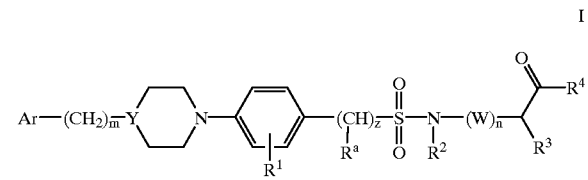

wherein:
  Ar is selected from phenyl;
    phenyl substituted with alkyl, —$NO_2$, halogen, —$OR^5$, —CN, —$CO_2R^5$, —$SO_3R^5$, —CHO, —$COR^5$, —$CONHR^5$, —$NHR^5$ or —$NHCOR^5$;
    heteroaryl; or
    2-naphthyl;
  $R^1$ is hydrogen, methyl, —$NO_2$, —Cl, —$NH_2$, —$NHCO_2CH_3$, —OH, or —$CO_2H$;
  $R^2$, $R^3$, and $R^a$ are the same or different and are independently selected from hydrogen, alkyl, —$(CH_2)_v$-aryl, —(CH$_2$)$_v$-heteroaryl, —(CH$_2$)$_v$-cycloalkyl, —(CH$_2$)$_p$—X—(CH$_2$)$_q$-aryl, —(CH$_2$)$_p$—X—(CH$_2$)$_q$-heteroaryl, —(CH$_2$)$_t$NR$^6$R$^{6a}$, —(CH$_2$)$_v$R$^7$, —(CH$_2$)$_v$CO$_2$R$^5$, —(CH$_2$)$_v$CONR$^6$R$^{6a}$, or —(CH$_2$)$_v$SR$^5$;

m is zero or 1;

Y is CH or N; provided that when m=1, Y does not=N;

z is zero or 1;

W is —CHR$^8$;

n is zero or 1;

R$^4$ is —OH, —NR$^6$R$^{6a}$, or —NHOR$^9$;

R$^5$ is hydrogen or alkyl;

v is 1 to 5;

X is O or S;

p and q are independently 1 to 5, provided that p+q is not greater than 5;

t is 1 to 9;

R$^6$ and R$^{6a}$ are each the same or different and are hydrogen or alkyl;

R$^7$ is 1,3-dihydro-1,3-dioxo-2H-isoindol-2-yl, or 1,3-dihydro-1,3-dioxo-benzo[f]isoindol-2-yl;

R$^8$ is hydrogen or alkyl; and

R$^9$ is hydrogen, alkyl, or benzyl; or a pharmaceutically acceptable salt thereof.

In a preferred embodiment, the present invention provides compounds of Formula I wherein:

Ar is phenyl;

m is 0 or 1;

Y is CH or N;

R$^1$ is hydrogen;

Z is zero;

R$^2$ is hydrogen or alkyl;

R$^3$ is hydrogen, alkyl, —(CH$_2$)$_n$-aryl, or —(CH$_2$)$_n$-heteroaryl;

R$^4$ is —OH or —NHOH;

n is 0 or 1; and

W is —CH$_2$—; or a pharmaceutically acceptable salt thereof.

In other preferred embodiments of the present invention relating to the compounds of Formula I, Z is zero, or Ar is phenyl, or Y is C, or m is zero, or R$^2$ is hydrogen, or R$^1$ is hydrogen, or n is zero, or R$^4$ is —OH, and pharmaceutically acceptable salts of these compounds provided that when m=1, Y does not=N.

In a most preferred embodiment, the compounds of Formula I are:

[4-(4-Phenyl-piperidin-1-yl)-benzenesulfonylamino]-acetic acid;

N-Hydroxy-2-[4-(4-phenyl-piperidin-1-yl)-benzenesulfonylamino]-acetamide;

3-[4-(4-Phenyl-piperidin-1-yl)-benzenesulfonylamino]-propionic acid;

(R)-4-Methyl-2-[4-(4-phenyl-piperidin-1-yl)-benzenesulfonylamino]-pentanoic acid;

(S)-4-Methyl-2-[4-(4-phenyl-piperidin-1-yl)-benzenesulfonylamino]-pentanoic acid;

(S)-3-Phenyl-2-[4-(4-phenyl-piperidin-1-yl)-benzenesulfonylamino]-propionic acid;

(R)-3-Phenyl-2-[4-(4-phenyl-piperidin-1-yl)-benzenesulfonylamino]-propionic acid;

(S)-3-(1H-Indol-3-yl)-2-[4-(4-phenyl-piperidin-1-yl)-benzenesulfonylamino]-propionic acid;

(±)-5-Phenyl-2-[4-(4-phenyl-piperidin-1-yl)-benzenesulfonylamino]-pentanoic acid;

[4-(4-Phenyl-piperazin-1-yl)-benzenesulfonylamino]-acetic acid;

{Isobutyl-[4-(4-phenyl-piperidin-1-yl)-benzenesulfonyl]amino}-acetic acid;

(S)-4-Phenyl-2-[4-(4-phenyl-piperidin-1-yl)-benzenesulfonylamino]-butyric acid;

(R)-2-[4-(4-Phenyl-piperidin-1-yl)-benzenesulfonylamino]-3-tritylsulfanyl-propionic acid sodium salt;

(R)-3-(1H-Indol-3-yl)-2-[4-(4-phenyl-piperidin-1-yl)-benzenesulfonylamino]-propionic acid, disodium salt, monohydrate;

(S)-2-{4-[-4-(4-Hydroxy-phenyl)-piperazin-1-yl]-benzenesulfonylamino}-3-phenyl-propionic acid;

(S)-2-{4-[-4-(4-Chloro-phenyl)-piperazin-1-yl]-benzenesulfonylamino}-3-phenyl-propionic acid, hydrochloride;

(R)-3-Mercapto-2-[4-(4-phenyl-piperidin-1-yl)-benzenesulfonylamino]-propionic acid, trifluoroacetic acid salt;

(S)-2-[4-(4-Benzyl-piperidin-1-yl)-benzenesulfonylamino]-3-phenyl-propionic acid;

(S)-3-(4-Benzyloxy-phenyl)-2-[4-(4-phenyl-piperidin-1-yl)-benzenesulfonylamino]-propionic acid;

(S)-3-(4-Hydroxy-phenyl)-2-[4-(4-phenyl-piperidin-1-yl)-benzenesulfonylamino]-propionic acid;

(S)-3-Phenyl-2-[4-(4-phenyl-piperazin-1-yl)-benzenesulfonylamino]-propionic acid;

(S)-2-{4-[-4-(3-Methoxy-phenyl)-piperazin-1-yl]-benzenesulfonylamino}-3-phenyl-propionic acid;

(S)-2-{4-[-4-(3-Hydroxy-phenyl)-piperazin-1-yl]-benzenesulfonylamino}-3-phenyl-propionic acid hydrobromide; and (S)-2-{4-[-4-(4-Methoxy-phenyl)-piperazin-1-yl]-benzenesulfonylamino}-3-phenyl-propionic acid.

The present invention also provides a method of inhibiting a matrix metalloproteinase, the method comprising administering to a patient in need of matrix metalloproteinase inhibition a matrix metalloproteinase inhibiting amount of a compound of Formula I.

In a preferred embodiment, the matrix metalloproteinase is stromelysin-1 or gelatinase-A.

In another embodiment, the present invention provides a method of preventing atherosclerotic plaque rupture comprising administering to a patient suffering from an atherosclerotic plaque a therapeutically effective amount of a compound of Formula I.

In another embodiment, the present invention provides a method of inhibiting aortic aneurism comprising administering to a patient having an aortic aneurism a therapeutically effective amount of a compound of Formula I.

In another embodiment, the present invention provides a method of preventing restenosis comprising administering to a patient following balloon angioplasty, graft or shunt implantation, or atherectomy, a therapeutically effective amount of a compound of Formula I.

In another embodiment, the present invention provides a method of treating periodontal disease comprising administering to a patient suffering therefrom a therapeutically effective amount of a compound of Formula I.

In another embodiment, the present invention provides a method of treating burns comprising administering to a patient suffering therefrom a therapeutically effective amount of a compound of Formula I.

In another embodiment, the present invention provides a method of treating decubital ulcers comprising administering to a patient suffering therefrom a therapeutically effective amount of a compound of Formula I.

In another embodiment, the present invention provides a method of treating chronic ulcers or wounds comprising administering to a patient suffering therefrom a therapeutically effective amount of a compound of Formula I.

In another embodiment, the present invention provides a method of treating cancer comprising administering to a patient suffering therefrom a therapeutically effective amount of a compound of Formula I.

In another embodiment, the present invention provides a method of treating multiple sclerosis comprising administering to a patient suffering therefrom a therapeutically effective amount of a compound of Formula I.

In another embodiment, the present invention provides a method of treating arthritis comprising administering to a patient suffering therefrom a therapeutically effective amount of a compound of Formula I.

In another embodiment, the present invention provides a method of treating autoimmune or inflammatory disorder dependent upon tissue invasion by leukocytes comprising administering to a patient suffering from an autoimmune or inflammatory disorder dependent upon tissue invasion by leukocytes a therapeutically effective amount of a compound of Formula I.

In another embodiment, the present invention provides a pharmaceutical composition comprising a compound of Formula I and a pharmaceutically acceptable carrier.

DETAILED DESCRIPTION OF THE INVENTION

The present invention provides compounds having the Formula I

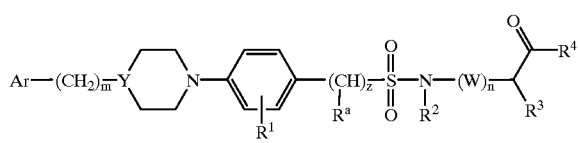

wherein:
Ar is selected from phenyl;
  phenyl substituted with alkyl, —$NO_2$, halogen, —$OR^5$, —CN, —$CO_2R^5$, —$SO_3R^5$, —CHO, —$COR^5$, —$CONHR^5$, —$NHR^5$, or —$NHCOR^5$;
  heteroaryl; or
  2-naphthyl;
$R^1$ is hydrogen, methyl, —$NO_2$, —Cl, —$NH_2$, —$NHCO_2CH_3$, —OH, or —$CO_2H$;
$R^2$ and $R^3$ are the same or different and are independently selected from hydrogen, alkyl, —$(CH_2)_v$-aryl, —$(CH_2)_v$-heteroaryl, —$(CH_2)_v$-cycloalkyl, —$(CH_2)_p$—X—$(CH_2)_q$-aryl, —$(CH_2)_p$—X—$(CH_2)_q$-heteroaryl, —$(CH_2)_t NR^6 R^{6a}$, —$(CH_2)_v R^7$, —$(CH_2)_v CO_2R^5$, —$(CH_2)_v CONR^6 R^{6a}$, or —$(CH_2)_v SR^5$;
m is zero or 1;
Y is CH or N; provided that when m 1, Y does not=N;
z is zero or 1;
W is —$CHR^8$;
n is zero or 1;
$R^4$ is —OH, —$NR^6 R^{6a}$, or —$NHOR^9$;
$R^5$ is hydrogen or alkyl;
v is 1 to 5;

X is O or S;
p and q are independently 1 to 5, provided that p+q is not greater than 5;
t is 1 to 9;
$R^6$ and $R^{6a}$ are each the same or different and are hydrogen or alkyl;
$R^7$ is 1,3-dihydro-1,3-dioxo-2H-isoindol-2-yl, or 1,3-dihydro-1,3-dioxo-benzo[f]isoindol-2-yl;
$R^8$ is hydrogen or alkyl; and
$R^9$ is hydrogen, alkyl, or benzyl; or
a pharmaceutically acceptable salt thereof.

In a preferred embodiment, the present invention provides compounds of Formula I wherein:
Ar is phenyl;
m is 0 or 1;
Y is CH or N;
$R^1$ is hydrogen;
Z is zero;
$R^2$ is hydrogen or alkyl;
$R^3$ is hydrogen, alkyl, —$(CH_2)_n$-aryl, or —$(CH_2)n$-heteroaryl;
$R^4$ is —OH or —NHOH;
n is 0 or 1; and
W is —$CH_2$—; or
a pharmaceutically acceptable salt thereof, provided that when m=1, Y does not=N.

The term "alkyl" means a straight or branched chain hydrocarbon radical having from 1 to 8 carbon atoms. Representative examples of alkyl groups include, but are not limited to, methyl, ethyl, n-propyl, isopropyl, n-butyl, sec-butyl, tert-butyl, isobutyl, n-pentyl, n-hexyl, n-heptyl and n-octyl.

The term "alkoxy" and "thioalkoxy" mean O-alkyl or S-alkyl having from 1 to 6 carbon atoms. Examples of alkoxy groups include, but are not limited to, methoxy, ethoxy, propoxy, isopropoxy, and butoxy.

The term "cycloalkyl" means a saturated hydrocarbon ring having 3 to 8 carbon atoms. Examples of cycloalkyl groups include, but are not limited to, cyclopropyl, cyclobutyl, cyclopentyl, cyclohexyl, cycloheptyl, and cyclooctyl.

The term "aryl" means an aromatic radical. For example, the aryl group can be a phenyl group, or a phenyl group substituted with 1 to 4 substituents (phenyl is abbreviated "Ph"). The substituents can be the same or different and can be selected from alkyl, alkoxy, thioalkoxy, hydroxy, halogen, trifluoromethyl, amino, alkylamino, dialkylamino, —$NO_2$, —CN, —$CO_2H$, —$CO_2$alkyl, —$SO_3H$, —CHO, —COalkyl, —$CONH_2$, —CONH-alkyl, —$CONHR^5$, —CON(alkyl)$_2$, —$(CH_2)_n$—$NH_2$, where n is 1 to 5, —$(CH_2)_n$—NH-alkyl, —$NHR^5$, or —$NHCOR^5$.

The term "heteroaryl" means an aromatic compound that includes one or more heteroatom. Examples of heteroatoms include O, S, and N. Examples of heteroaryl groups are 2- or 3-thienyl, 2- or 3-furanyl, 2- or 3-pyrrolyl, 2-, 3- or 4-pyridinyl, 2-pyrazinyl, 1H-indol-6-yl, 1H-indol-5-yl, 1H-benzimidazol-5-yl, or 1H-benzimidazol-6-yl.

The term "halogen" means fluorine, chlorine, bromine, or iodine.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma Sci.,* 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma Sci.,* 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

Also provided by the present invention is a method of inhibiting a matrix metalloproteinase, the method comprising administering to a patient in need of matrix metalloproteinase inhibition a matrix metalloproteinase inhibiting amount of a compound of Formula I. In a preferred embodiment, the matrix metalloproteinase is stromelysin-1 or gelatinase-A.

The term "patient" means humans and other animals.

A patient in need of matrix metalloproteinase inhibition is a patient who may suffer from atherosclerotic plaque rupture or restenosis, or a patient who suffers from aortic aneurism, periodontal disease, burns, decubital ulcers, chronic ulcers or wounds, cancer, arthritis, multiple sclerosis, or other autoimmune or inflammatory disorders dependent upon tissue invasion by leukocytes.

Also provided by the present invention is a method of preventing atherosclerotic plaque rupture comprising administering to a patient suffering from an atherosclerotic plaque a therapeutically effective amount of a compound of Formula I.

Also provided by the present invention is a method of inhibiting aortic aneurism comprising administering to a patient having an aortic aneurism a therapeutically effective amount of a compound of Formula I.

Also provided by the present invention is a method of preventing restenosis comprising administering to a patient following balloon angioplasty, graft or shunt implantation or atherectomy, a therapeutically effective amount of a compound of Formula.

Also provided by the present invention is a method of treating periodontal disease comprising administering to a patient suffering therefrom a therapeutically effective amount of a compound of Formula I.

Also provided by the present invention is a method of treating burns comprising administering to a patient suffering therefrom a therapeutically effective amount of a compound of Formula I.

Also provided by the present invention is a method of treating decubital ulcers comprising administering to a patient suffering therefrom a therapeutically effective amount of a compound of Formula I.

Also provided by the present invention is a method of treating chronic ulcers or wounds comprising administering to a patient suffering therefrom a therapeutically effective amount of a compound of Formula I.

Also provided by the present invention is a method of treating cancer metastasis comprising administering to a patient suffering therefrom a therapeutically effective amount of a compound of Formula I.

Also provided by the present invention is a method of treating arthritis comprising administering to a patient suffering therefrom a therapeutically effective amount of a compound of Formula I.

Also provided by the present invention is a method of treating multiple sclerosis comprising administering to a patient suffering therefrom a therapeutically effective amount of a compound of Formula I.

Also provided by the present invention is a method of treating an autoimmune or inflammatory disorder dependent upon tissue invasion by leukocytes comprising administering to a patient suffering from an autoimmune or inflammatory disorder dependent upon tissue invasion by leukocytes a therapeutically effective amount of a compound of Formula I.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, burns, decubital ulcers, chronic ulcers or wounds, cancer, multiple sclerosis, arthritis, or other autoimmune or inflammatory disorders dependent upon tissue invasion by leukocytes, the compounds utilized in the pharmaceutical method of this invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following examples illustrate particular embodiments of the invention and are not intended to limit the specification, including the claims, in any way.

EXAMPLES

A compound of Formula I can be made by the general route, as set forth in Scheme I below.

With reference to Scheme I, a compound of Formula II is reacted with a compound of Formula III (commercially available from Sigma Chemical Company, St. Louis, Mo., or can be synthesized according to Schemes V and VI) in the presence of a suitable base such as triethylamine, sodium carbonate or potassium carbonate in a suitable solvent such as water,. methanol, tetrahydrofuran, or some combination thereof, at temperatures between 0° C. and 50° C. to obtain a compound of Formula IV. The compound of Formula IV is then reacted with a compound of Formula V in the presence of an excess of a suitable base such as sodium carbonate or potassium carbonate in a suitable solvent such as dimethylsulfoxide (DMSO) or dimethylformamide (DMF) at temperatures between 25° C. and 180° C. to obtain a compound of Formula Ia, wherein the variables are defined as above, except that z=0 and $R^4$=OH.

Specific compounds of the present invention can be prepared by various routes, all of which are well known in the art.

SCHEME I

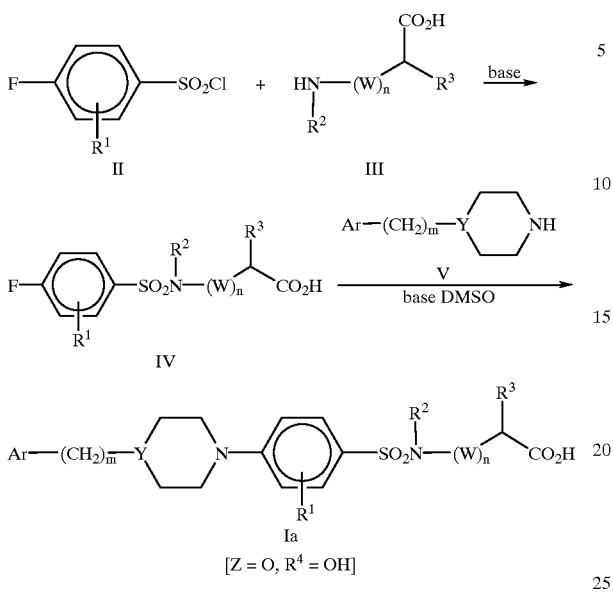

Compounds of Formula I wherein z=n=0, $R^1$ and $R^2$ are hydrogen, Y=CH, $R^4$=OH, and Ar, m and $R^3$ are as defined in Formula I, can be prepared according to the sequence described in Scheme II below.

With regard to Scheme II, the halide (1), wherein halo is defined as iodine, bromine or chlorine, is reacted with a suitable metallating agent (M), such as an alkyl lithium, for example, n-butyl lithium, sec-butyl lithium, or tert-butyl lithium, or magnesium metal, in a suitable solvent such as tetrahydrofuran (THF) or diethyl ether ($Et_2O$) at temperatures between −80° C. and 60° C., followed by 1-(phenylmethyl)-4-piperidinone at temperatures between −80° C. and 25° C. to obtain the 4-piperidinol (2). The 4-piperidinol (2) is dehydrated by stirring in a suitable solvent such as acetic acid (AcOH) with a strong acid catalyst such as concentrated hydrochloric acid (HCl) at temperatures between 0° C. and reflux to obtain the 1,2,5,6-tetrahydropyridine (3) as an acid salt. The 1,2,5,6-tetrahydropyridine (3) is reduced by catalytic reduction using a suitable catalyst such as 10% palladium on carbon (Pd/C) and hydrogen gas ($H_2$) at pressures between 10 p.s.i. and 100 p.s.i. in a suitable solvent such as absolute ethanol, acetic acid, or tetrahydrofuran to yield the piperidine hydrochloride (4).

The sulfonamide (6) wherein $R^3$ is as defined in Formula I, may be prepared by reacting the amino acid (5) which is commercially available from a variety of vendors, e. g., Sigma Chemical Company, St. Louis, Mo., or synthesized by standard methods well known in the art, (set forth in Schemes V & VI below) with 4-fluoro-benzenesulfonyl chloride in the presence of a suitable base such as triethylamine, sodium carbonate ($Na_2CO_3$) or potassium carbonate in a suitable solvent such as water, methanol, tetrahydrofuran, at temperatures between 0° C. and 50° C.

The piperidine hydrochloride (4) is reacted with the sulfonamide (6) in the presence of an excess of a suitable base such as sodium carbonate or potassium carbonate in a suitable solvent such as dimethylsulfoxide or dimethylformamide at temperatures between 25° C. and 180° C. to obtain the (sulfonylamino)-carboxylic acid (7).

SCHEME II

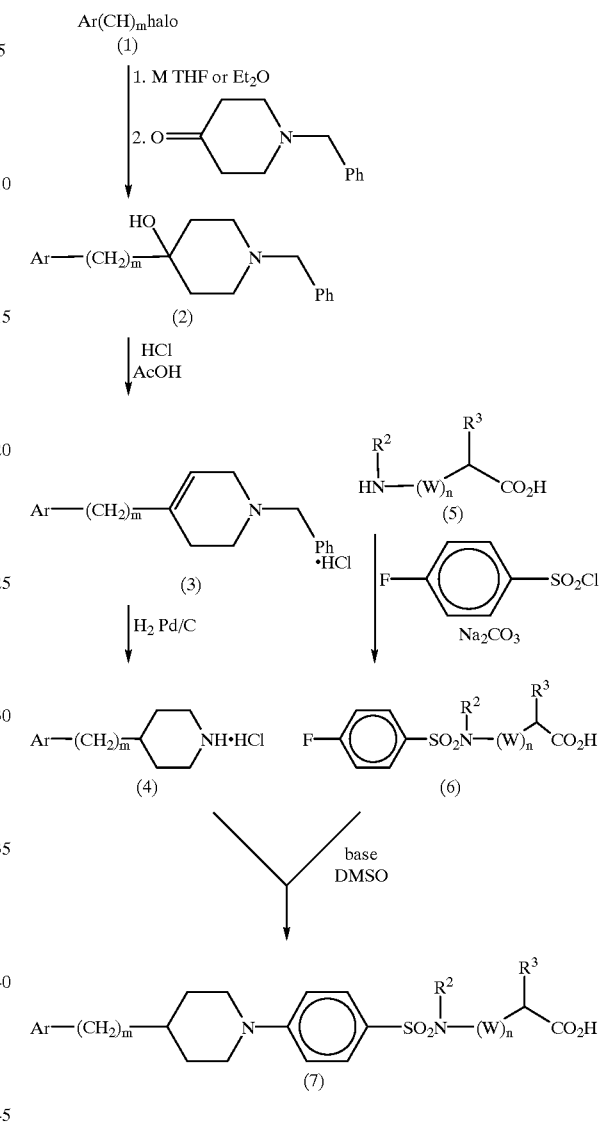

Compounds of Formula I wherein z=n=0, $R^1$ and $R^2$ are hydrogen, Y=CH, $R^4$=$NHOR^9$ or $NR^6R^{6a}$, and Ar, m and $R^3$ are as defined in Formula I, can be prepared according to the sequence described in Scheme III.

With regard to Scheme III, the (sulfonylamino)-carboxylic acid (7) can be reacted with a suitable O-substituted hydroxylamine hydrochloride of the formula $H_2NOR^9$.HCl in the presence of a suitable base such as triethylamine ($Et_3N$) or N,N-diisopropyl-N-ethylamine and a suitable coupling agent such as 1,1'-carbonyldi-imidazole (CDI) or N,N'-dicyclohexylcarbodiimide (DCC) and 1-hydroxybenzo-triazole (HOBT) in a suitable solvent such as tetrahydrofuran (THF), dichloromethane, or N,N-dimethyl-formamide (DMF) at temperatures between 0° C. and 100° C. to yield the O-substituted hydroxamic acid (8). When $R^9$ is defined as benzyl ($R^9$=$CH_2Ph$), the O-substituted-hydroxamic acid (8) can be reduced to yield the hydroxamic acid (9) by catalytic reduction using hydrogen gas at pressures between 10 p.s.i. and 100 p.s.i. and a suitable catalyst such as 5% or 10% palladium on barium sulfate in a suitable solvent such as THF or ethanol. Alternatively, the (sulfonylamino)-carboxylic acid (7) can be reacted with various amines of the formula $R^6R^{6a}NH$ in the presence of a suitable coupling agent such as 1,1'-carbonyldiimidazole (CDI) or N,N'-dicyclohexylcarbodiimide (DCC) and 1-hydroxybenzotriazole (HOBT) in a suitable solvent such as tetrahydrofuran, dichloromethane, or N,N-dimethylformamide at temperatures between 0° C. and 100° C. to yield the (sulfonylamino)-carboxamides (10).

Compounds of Formula I wherein z=m=n=0, $R^1$ and $R^2$ are hydrogen, Y=N, and Ar, $R^3$, and $R^4$, are as defined in Formula I, can be synthesized according to the sequence described in Scheme IV below.

With regard to Scheme IV, the amine (11) is reacted with bis(2-chloroethyl)amine hydrochloride of the formula $HN(CH_2CH_2Cl)_2 \cdot HCl$, in a suitable solvent such as chlorobenzene, at temperatures between 25° C. and 180° C. to yield the piperazine hydrochloride (12). The piperazine hydrochloride (12) is reacted with the sulfonamide (6) in a manner similar to that previously described for compound (7) to obtain the corresponding piperazine-carboxylic acid (13). The piperazine-carboxylic acid (13) can be reacted with a suitable O-substituted hydroxylamine hydrochloride of the formula $H_2NOR^9 \cdot HCl$ in the presence of a suitable base such as triethylamine ($Et_3N$) or N,N-diisopropyl-N-ethylamine and a suitable coupling agent such as 1,1'-carbonyldi-imidazole (CDI) or N,N'-dicyclohexylcarbodiimide (DCC) and 1-hydroxybenzotriazole (HOBT) in a suitable solvent such as tetrahydrofuran (THF), dichloromethane, or N,N-dimethylformamide (DMF) at temperatures between 0° C. and 100° C. to yield the O-substituted-hydroxamic acid (14). Alternatively, the piperazine-carboxylic acid (13) can be converted to the free hydroxamic acid (15) by first reacting with a suitable activating agent such as isobutyl chloroformate of formula $(CH_3)_2CHCH_2COCl$ in the presence of a suitable base such as triethylamine or N,N-diisopropyl-N-ethylamine in a suitable solvent such as dichloromethane or tetrahydrofuran at temperatures between -78° C. and +25° C. followed by a suitable O-substituted-hydroxylamine such as O-(trimethylsilyl)-hydroxylamine of formula $H_2NOSi(CH_3)_3$ (TMSONH$_2$) or O-(tert-butyldimethylsilyl)-hydroxylamine of formula $H_2NOSi(CH_3)_2C(CH_3)_3$ and then quenching the reaction with aqueous acid. Alternatively, the piperazine-carboxylic acid (13) can be reacted with various amines of the formula $HNR^6R^{6a}$ in the presence of a suitable coupling agent such as 1,1'-carbonyldiimidazole (CDI) or N,N'-dicyclohexylcarbodiimide (DCC) and 1-hydroxybenzotriazole (HOBT) in a suitable solvent such as tetrahydrofuran, dichloro-methane, or N,N-dimethylformamide at temperatures between 0° C. and 100° C. to yield the piperazine-carboxamides (16).

SCHEME III

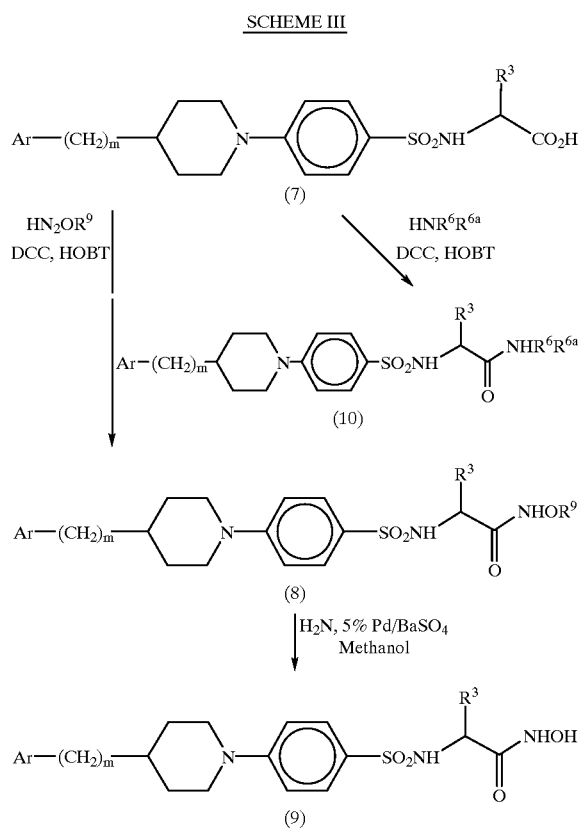

SCHEME IV

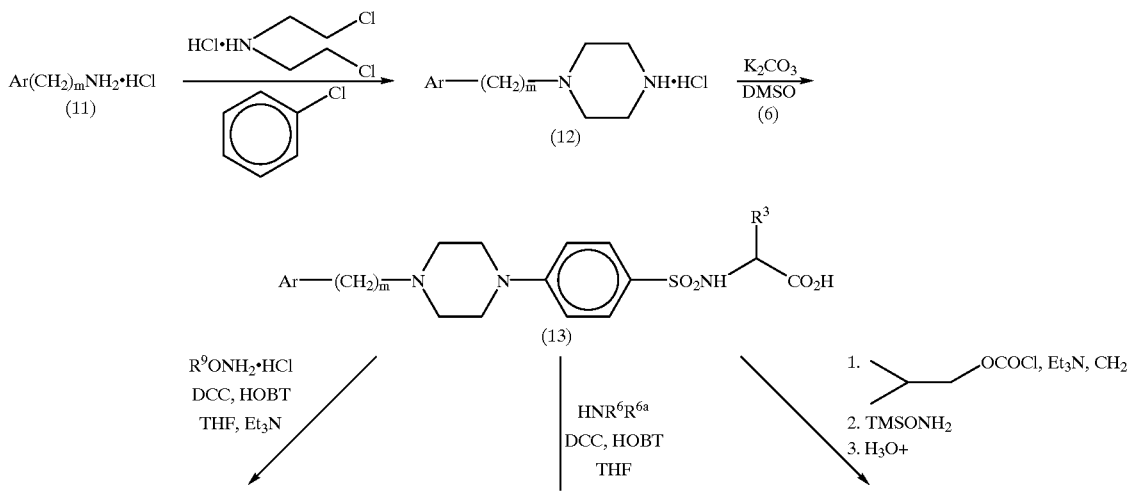

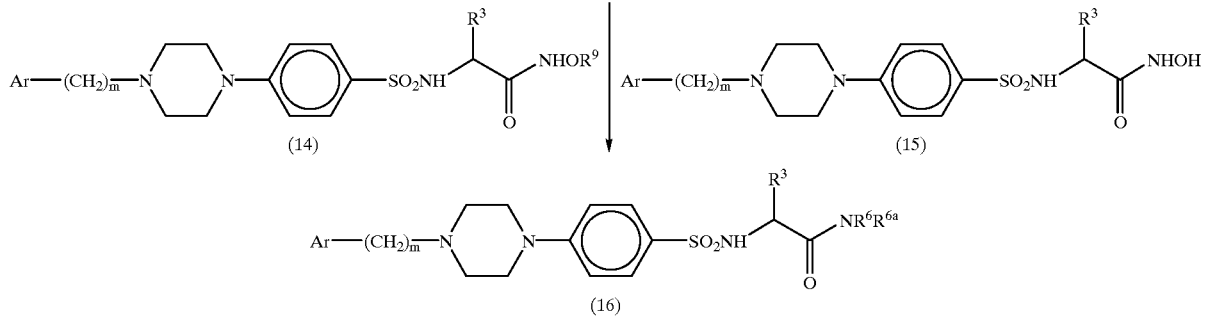

Compounds of Formula I wherein z=0, n=1, $R^1$ is hydrogen, and Ar, Y, $R^2$, $R^3$, $R^4$, and $R^8$ are as defined in Formula I can be prepared as set forth in Scheme V below.

With regard to Scheme V, an aldehyde (17) is reacted with trimethylphosphono-acetate of formula $(CH_3O)_2P(O)CH_2CO_2CH_3$ in the presence of a suitable base such as sodium hydride or lithium diisopropylamide (LDA) in a suitable solvent such as tetrahydrofuran at temperatures between −78° C. and +60° C. to yield the unsaturated ester (18). The unsaturated ester (18) is reacted with lithium (R)-(+)-N-benzyl-N-α-methylbenzylamine, prepared in situ by a slow addition of n-butyl lithium to (R)-(+)-N-benzyl-N-α-methylbenzylamine, in a suitable solvent such as tetrahydrofuran at −78° C. followed by the addition of $R^3$-halo wherein halo is defined as chlorine, bromine, or iodine, and $R^3$ is as defined in Formula I, and allowing the temperature to slowly warm from −78° C. to +25° C. overnight to yield the amino ester (19). (The * designates a chiral carbon.) The diastereomers of the amino ester (19) can be separated by column chromatography. The complimentary diastereomer of the amino ester (19) can be prepared by following the procedure described previously and substituting (S)-(−)-N-benzyl-N-α-methylbenzylamine for (R)-(+)-N-benzyl-N-α-methylbenzylamine. The single stereoisomers of amino ester (19) can be reduced separately by reacting with hydrogen gas in the presence of a suitable catalyst such as 5% to 30% palladium on carbon in a suitable solvent such as tetrahydrofuran, acetic acid, methanol, or mixtures thereof at pressures between atmospheric and 100 p.s.i. and temperatures between 25° C. and 100° C. to yield the amino ester (20). The amino ester (20) is then reacted in a suitable aqueous acid mixture such as 6 M hydrochloric acid at temperatures between 25° C. and reflux to yield the amino acid hydrochloride (21). Alternatively, the amino ester (20) can be reacted with an alkyl halide of formula $R^2$-halo, wherein $R^2$ is as defined in Formula I and halo is defined as chlorine, bromine, or iodine, in the presence of a suitable base such as triethylamine or N,N-diisopropyl-N-ethylamine in a solvent such as diethyl ether or tetrahydrofuran at temperatures between 0° C. and 50° C. followed by conversion of the free amino ester to the amino ester hydrochloride (22). The amino ester hydrochloride (22) is then reacted in a suitable aqueous acid mixture such as 6 M hydrochloric acid following the procedure described above to yield the amino acid hydrochloride (23). When in the procedure described by Scheme II, the amino acid hydrochlorides (21) or (23) are substituted for the amino acid (5) and reacted with 4-fluoro-benzenesulfonyl chloride, the sulfonamides (24) and (25) can be prepared, respectively. When in the procedures described for Schemes II and IV the sulfonamides (24) or (25) are substituted for the sulfonamide (6) and reacted with either the piperidine hydrochloride (4) or the piperazine hydrochloride (12) (generically represented by V), respectively, the (sulfonylamino)-carboxylic acids (26) and (27) can be prepared, respectively. When in the procedures described for Schemes III and IV the (sulfonylamino)-carboxylic acids (26) and (27) are substituted for the (sulfonylamino)-carboxylic acids (7) or (13) and the appropriate methodology for either the piperidines (Scheme III) or piperazines (Scheme IV) is followed, the compounds (28) and (29) can be prepared, respectively.

SCHEME V

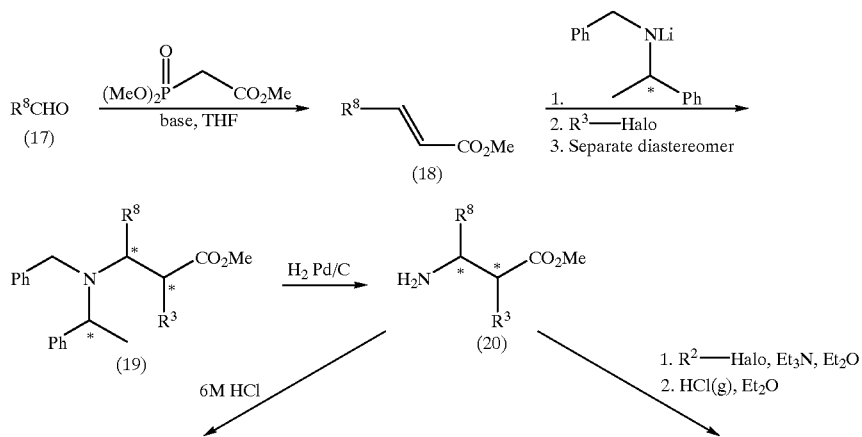

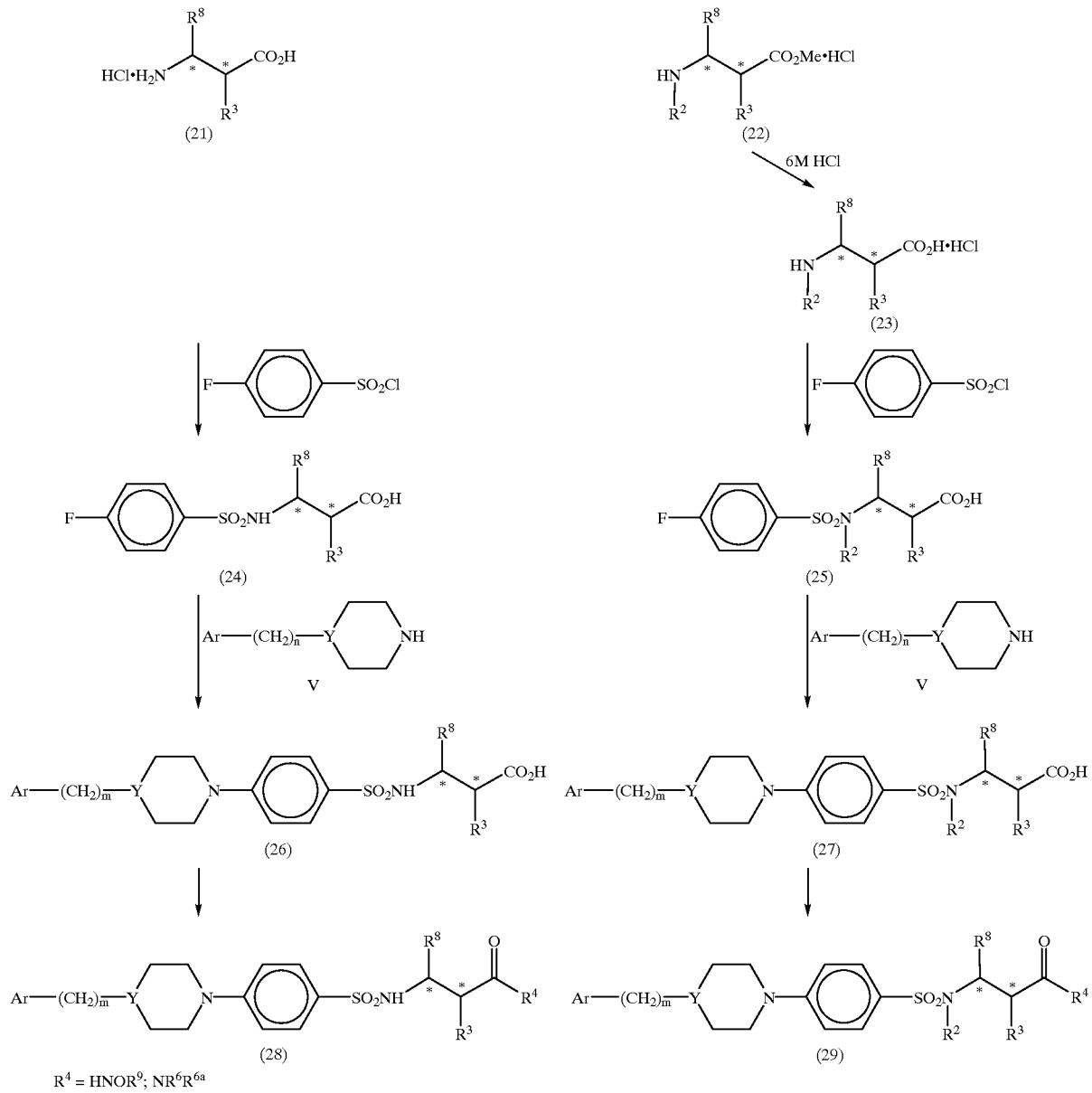

Compounds of Formula I wherein z=n=0, $R^1$ is hydrogen, and Ar, m, Y, $R^2$, $R^3$, and $R^4$ are as defined in Formula I, can be synthesized according to the sequence described in Scheme VI below.

With regard to Scheme VI, an amine of formula $R^2NH_2$, wherein $R^2$ is as defined in Formula I, is reacted with a bromo-ester (30), wherein $R^3$ is as defined in Formula I, in the presence of a suitable base such as triethylamine ($Et_3N$) or N,N-diisopropyl-N-ethylamine in a solvent such as diethyl ether or tetrahydrofuran at temperatures between −10° C. and 50° C. to afford the free amino ester which is converted to the amino ester hydrochloride (31). Alternatively, the amino ester hydrochloride (31) can be prepared by reacting an alkyl halide of the formula $R^2$-halo, wherein $R^2$ is as defined in Formula I and halo is defined as chlorine, bromine, or iodine, with an amino-ester hydrochloride (30a), wherein $R^3$ is as defined in Formula I, following the procedure described for (31). The amino-ester hydrochloride (31) is reacted in a suitable aqueous acid mixture such as 6 M hydrochloric acid following the procedure described previously for Scheme V to yield the amino-acid hydrochloride (32). When in the procedure described for Scheme II the amino-acid hydrochloride (32) is substituted for the amino acid (5) and reacted with 4-fluoro-benzenesulfonyl chloride, the sulfonamide (33) is obtained. When in the procedures described for Schemes II and IV the sulfonamide (33) is substituted for the sulfonamide (6) and reacted with either the piperidine hydrochloride (4) or the piperazine hydrochloride (12), respectively, the (sulfonylamino)-carboxylic acid (34) can be prepared. When in the procedures described for Schemes III and IV the (sulfonylamino)-carboxylic acid (34) is substituted for either the (sulfonylamino)-carboxylic acid (7) or (13) and the appropriate methodology for either the piperidines (Scheme III) or piperazines (Scheme IV) is followed, the compound (35) can be prepared, where $R^4$ is defined as $NHOR^9$ or $NR^6R^{6a}$.

SCHEME VI

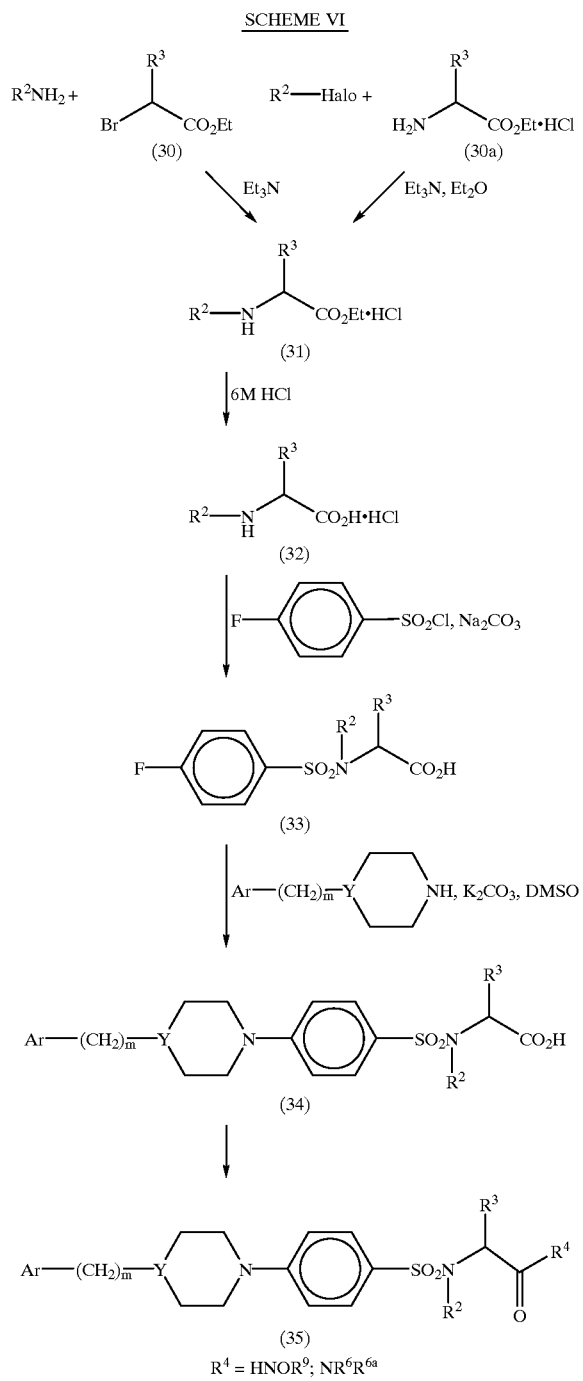

Compounds of Formula I wherein z=0, Ar, Y, m, n, $R^1$, $R^2$, and $R^3$ are as defined in Formula I, and $R^4$ is OH, can be synthesized according to the sequence described in Scheme VII below.

The commercially available fluorosulfonic acids (36) as their sodium salts are reacted with a suitable halogenating agent such as a mixture of phosphorus pentachloride ($PCl_5$) in phosphorus oxychloride ($POCl_3$) at temperatures between $-20°$ C. and $50°$ C. to yield the sulfonyl chloride (37). The sulfonyl chloride (37) is reacted with either the amino acid (5) from Scheme II, the amino acid hydrochloride (21) from Scheme V, the amino acid hydrochloride (23) from Scheme V, or the amino acid hydrochloride (32) from Scheme VI, all of which may be represented by the general structure designated by Formula III of Scheme I, in the presence of a suitable base such as triethylamine, sodium carbonate or potassium carbonate in a suitable solvent such as water, methanol, tetrahydrofuran or some combination thereof, at temperatures between $0°$ C. and $50°$ C. to give the (sulfonylamino)-carboxylic acid (38). When in the procedures described for Schemes II and IV the sulfonamide (38) is substituted for the sulfonamide (6) and reacted with either the piperidine hydrochloride (4) or the piperazine hydrochloride (12), respectively, represented by the general structure V, the (sulfonylamino)-carboxylic acid (40) can be prepared. When in the procedures described for Schemes III and IV the (sulfonylamino)-carboxylic acid (40) is substituted for either the (sulfonylamino)-carboxylic acid (7) or (13) and the appropriate methodology for either the piperidines (Scheme III) or piperazines (Scheme IV) is followed, the compound (40a) can be prepared, where $R^4$ is defined as $NHOR^9$ or $NR^6R^{6a}$.

SCHEME VII

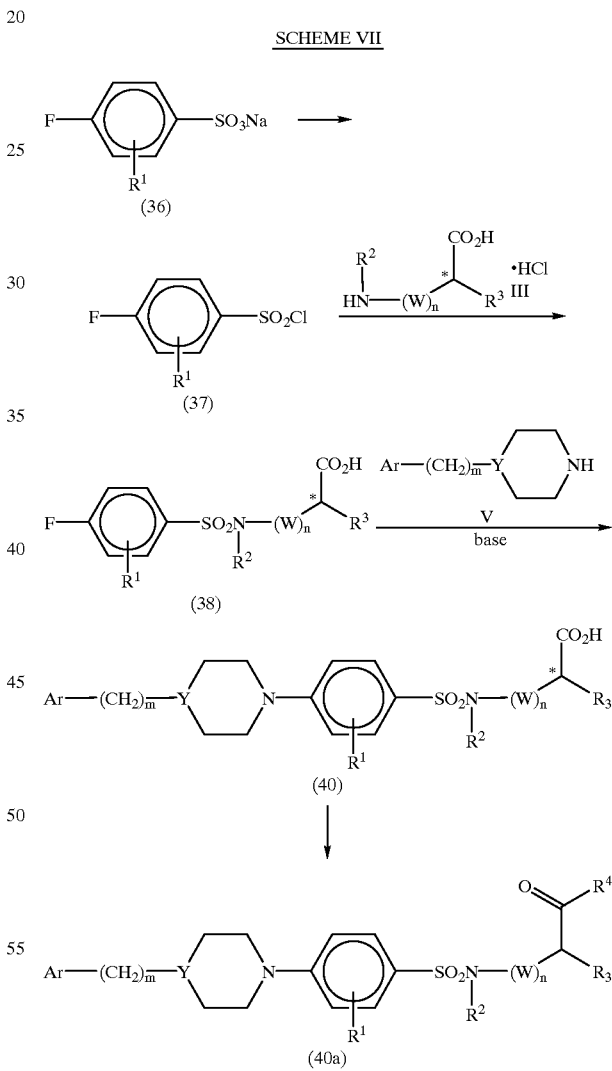

Compounds of Formula I wherein z=1, $R^1$ is hydrogen, and Ar, Y, $R^2$, $R^3$, $R^4$, W, m, and n are as defined in Formula I, can be prepared according to the sequence described in Scheme VIII.

With regard to Scheme VIII, the compound of Formula V is reacted with 4-fluorobenzoic acid, ethyl ester in the presence of an excess of a suitable base such as sodium carbonate ($Na_2CO_3$) or potassium carbonate in a suitable solvent such as dimethylsulfoxide (DMSO) or dimethylformamide at temperatures between 25° C. and 180° C. to obtain the ester (41). The ester (41) is reduced with a suitable reducing agent such as lithium aluminum hydride ($LiAlH_4$) in a suitable solvent such as tetrahydrofuran at temperatures between 0° C. and 60° C. to yield the alcohol (42). The alcohol (42) is reacted with a suitable halogenating agent such as phosphorous tribromide ($PBr_3$) in dichloromethane at temperatures between −40° C. and 40° C. to yield the halide (43). The halide (43) is reacted with sodium thiosulfate ($Na_2S_2O_3$) in water with or without a phase transfer agent such as N-methyl-N,N,N-tri(n-octyl)ammonium chloride at temperatures between 0° C. and 100° C. in the presence of chlorine gas ($Cl_2$) to yield the sulfonyl chloride (44). Alternatively, the halide (43) can be reacted with sodium thiosulfate ($Na_2S_2O_3$) in water with or without a phase transfer agent such as N-methyl-N,N,N-tri(n-octyl) ammonium chloride at temperatures between 25° C. and 100° C. to yield the sulfonate (45). The sulfonate (45) is then reacted with a suitable halogenating agent such as a mixture of phosphorus pentachloride ($PCl_5$) in phosphorus oxychloride ($POCl_3$) at temperatures between −20° C. and 150° C. to yield the sulfonyl chloride (44). The sulfonyl chloride (44) is reacted with either the amino acid (5) from Scheme II, the amino acid hydrochloride (21) from Scheme V, the amino acid hydrochloride (23) from Scheme V, or the amino acid hydrochloride (32) from Scheme VI, all of which may be represented by the general structure designated by Formula III of Scheme I, in the presence of a suitable base such as triethylamine, sodium carbonate or potassium carbonate in a suitable solvent such as water, methanol, tetrahydrofuran or some combination thereof, at temperatures between 0° C. and 50° C. to give the (sulfonylamino)-carboxylic acid (46). Alternatively, the sulfonyl chloride (44) can be reacted with tert-butylamine in a suitable solvent such as diethylether or tetrahydrofuran in the presence of excess base such as tert-butylamine or triethylamine to yield the sulfonamide (48). The sulfonamide (48) can be reacted with two equivalents of a strong base such as n-butyl lithium, sec-butyl lithium, or tert-butyl lithium in a suitable solvent such as tetrahydrofuran at temperatures between −78° C. to +25° C., followed by the addition of an alkyl halide of the formula $R^2$-halo, wherein $R^2$ is as defined in Formula I, and halo is defined as chlorine, bromine, or iodine, to yield the sulfonamide (49). The sulfonamide (49) can be reacted with a strong acid such as trifluoroacetic acid (TFA) either neat or in a suitable solvent such as dichloromethane to yield the sulfonamide (50). The sulfonamide (50) can be reacted with a suitable base such as sodium hydride (NaH) in tetrahydrofuran as solvent or sodium ethoxide in ethanol as solvent, followed by the addition of the bromoester (30), wherein $R^3$ is as defined in Formula I, to yield the (sulfonylamino)-ester (51). The (sulfonylamino)-ester (51) can be reacted with either lithium, sodium, or potassium hydroxide in a suitable solvent such as ethanol followed by acidification to yield the (sulfonylamino)-carboxylic acid (52).

When in the procedures described for Schemes III and IV, the (sulfonylamino)-carboxylic acids (46) or (52) is substituted for either the (sulfonylamino)-carboxylic acid (7) or (13) and the appropriate methodology for either the piperidines (Scheme III) or piperazines (Scheme IV) is followed, the compounds (47) and (53) can be prepared, where $R^4$ is defined as $NHOR^9$ or $NR^6R^{6a}$.

SCHEME VIII

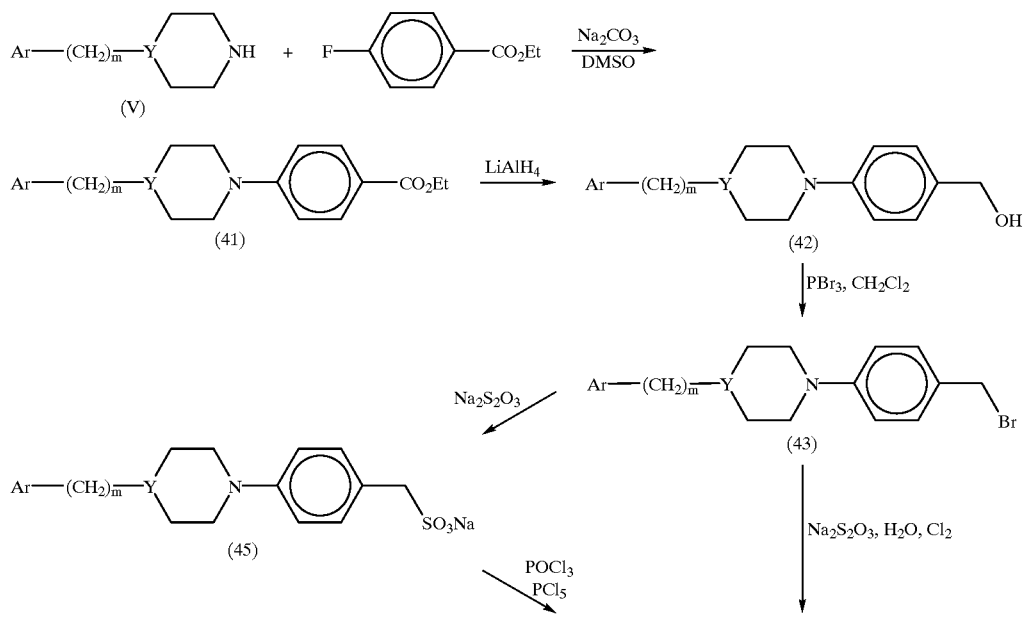

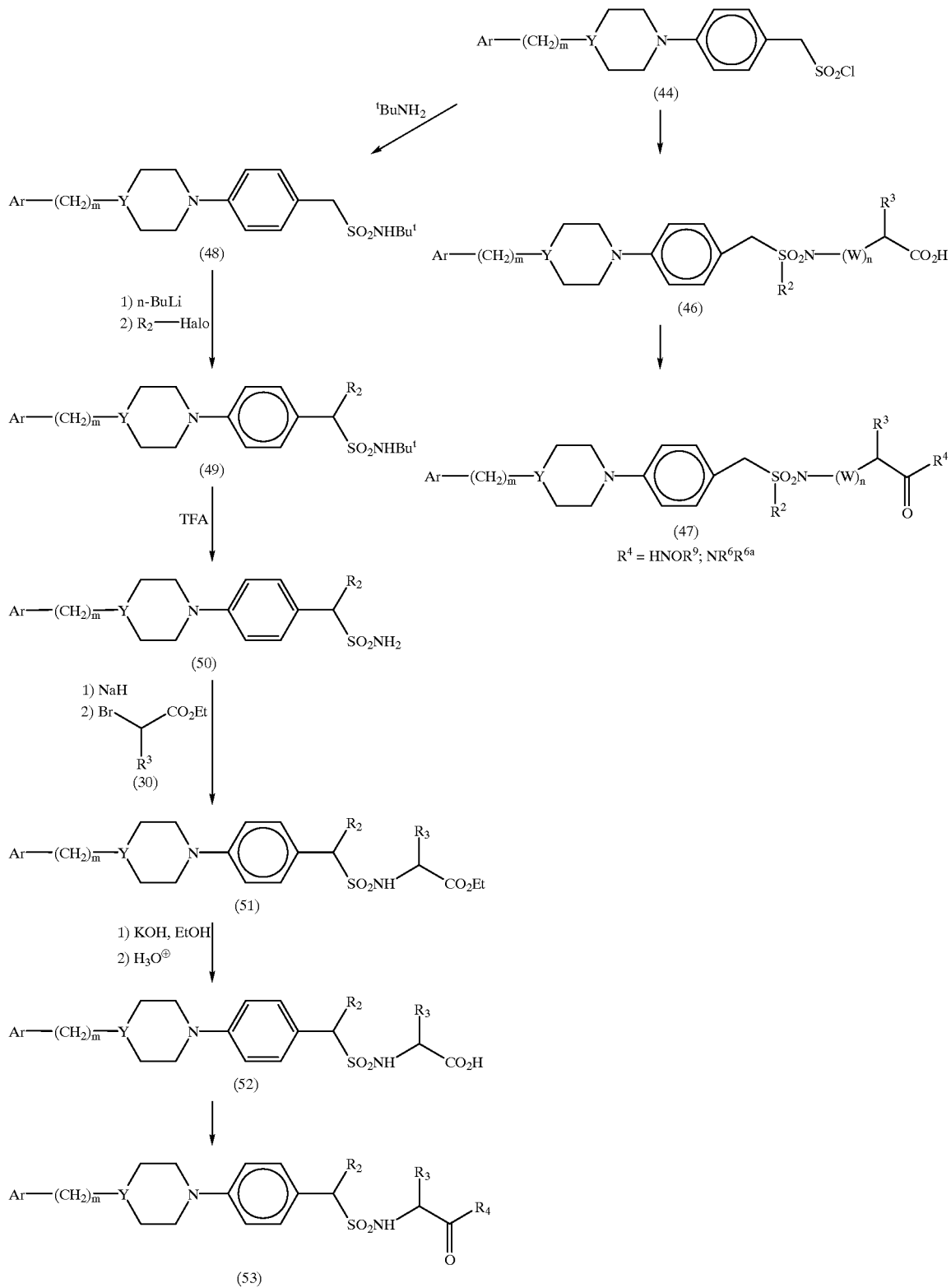

The O-substituted-hydroxylamine hydrochlorides of the formula H₂NOR⁹·HCl can be purchased from commercial sources or prepared as set forth in Scheme IX.

SCHEME IX

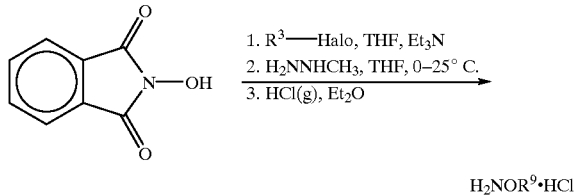

H$_2$NOR$^9$·HCl

Example 1

[4-(4-Phenyl-piperidin-1-yl)-benzenesulfonylamino]-acetic acid (a) (4-Fluoro-benzenesulfonylamino)-acetic acid A mixture of 4-fluoro-benzenesulfonyl chloride (9.68 g, 0.497 mol), glycine (4.48 g, 0.0598 mol), and sodium carbonate (16.99 g, 0.160 mol) in water (60 mL) was stirred at room temperature for 42 hours. The mixture was carefully acidified to pH 8 to 9 with concentrated hydrochloric acid, and washed 2 times with dichloromethane. The aqueous layer was acidified further to pH 2, and the resulting white suspension was extracted two times with ethyl acetate. The extracts were combined, washed with saturated sodium chloride solution, and dried over magnesium sulfate. The dried solution was rotary evaporated to give a white solid, which was dried in vacuo; yield 4.7 g (41%), mp=154.0–155.5° C.

(b) [4-(4-Phenyl-piperidin-1-yl)benzenesulfonyl-amino]-acetic acid

A stirred mixture of (4-fluoro-benzenesulfonyl-amino)-acetic acid (0.0895 g, 0.000384 mol), 4-phenyl-piperidine (0.618 g, 0.000383 mol), and potassium carbonate (0.109 g, 0.000789 mol) in dry dimethyl sulfoxide (0.10 mL) in a tightly capped vial was placed in a hot sand bath (115° C.). After 21 hours, the reaction mixture was cooled and partitioned between ethyl acetate and water. The mixture was acidified with 1M hydrochloric acid (3.2 mL, 0.0032 mol) and the layers were separated. The aqueous layer was washed with additional ethyl acetate. The organics were combined, dried (MgSO$_4$), and rotary evaporated to give a glass. The glass was dissolved in methanol, silica gel was added (4.2 g, 230–400 mesh), and the mixture was rotary evaporated to dryness. The resulting powder was poured onto a column of silica gel (14 g, 230–400 mesh), and eluted with a mixture of hexanes-ethyl acetate-acetic acid (15:15:1, 11×15 mL). Fractions containing product were combined and rotary evaporated. The residue was crystallized from methanol-water (1:1) after a hot filtration to give the title compound as a pale yellow solid; yield 0.070 g (49%), mp=154.5–155.5° C.

Example 2

N-Hydroxy-2-[4-(4-phenyl-piperidin-1-yl)-benzenesulfonylamino]-acetamide (a) N-[(Phenylmethyl)oxy]-2-[4-(4-phenyl-piperidin-1-yl)-benzenesulfonylamino]-acetamide A suspension of O-benzylhydroxylamine hydrochloride (0.110 g, 0.000689 mol) in a mixture of triethylamine (0.096 mL, 0.00069 mol) in anhydrous tetrahydrofuran (7 mL) was heated on a steam bath, and dimethylformamide (≈5 mL) was added until all solids had dissolved. The mixture was cooled to room temperature. The solids which precipitated were filtered off and set aside.

In a separate flask containing a cool (5° C.), stirred solution of [4-(4-phenyl-piperidin-1-yl)-benzenesulfonylamino]-acetic acid (0.2307 g, 0.0006161 mol) and 1-hydroxy-benzo-1,2,3-triazole (0.0842 g, 0.000623 mol) in anhydrous tetrahydrofuran (10 mL) was added in one portion 1,3-dicyclohexylcarbodiimide (0.1449 g, 0.000702 mol). The mixture was stirred for 30 minutes at 5° C. then allowed to warm to room temperature. After 3 hours at room temperature, the mixture was added in one portion to the filtrate containing O-benzylhydroxylamine. The mixture was stirred at room temperature for 16 hours, then refluxed (74° C.) for 1 hour. The volatiles were rotary evaporated off, and the residue was partitioned between ethyl acetate and water. The aqueous layer was extracted with ethyl acetate. The organics were combined, washed with 0.1 M NaOH, water, 0.1 M HCl, water, and saturated sodium chloride. The organic layer was dried (MgSO$_4$) and rotary evaporated. The residue was dissolved in chloroform, and chromatographed on silica gel (34 g, 230–400 mesh) eluting with dichloromethane-acetone (9:1, 10×30 mL). Fractions containing product were rotary evaporated to give a white solid. The solid was dried in vacuo; yield 0.1448 g (49%), mp=163–165° C.

(b) N-Hydroxy-2-[4-(4-phenyl-piperidin-1-yl)-benzenesulfonylamino]-acetamide

A room temperature mixture of N-[phenyl-methyl)oxy]-2-[4-(4-phenyl-piperidin-1-yl)-benzenesulfonylamino]-acetamide (0.1115 g, 0.0002325 mol) in methanol-tetrahydrofuran (1:1, 25 mL) was hydrogenated at 50 p.s.i. over 5% palladium on barium sulfate (0.018 g) for approximately 10 hours Additional catalyst (0.020 g) was added, and the mixture hydrogenated again for approximately 10 hours. The mixture was filtered through celite, and the filtrate was rotary evaporated to give a glaze. The glaze was dissolved in chloroform-methanol, silica gel (1.6 g, 230–400 mesh) was added, and the mixture was rotary evaporated to dryness. The powder was poured onto a column of silica gel (10 g, 230–400 mesh) and eluted with hexanes-ethyl acetate-acetic acid (10:20:1, 16×10 mL and 10:20:2, 16×10 mL). Fractions containing product were rotary evaporated, and the residue triturated with chloroform. The chloroform suspension was filtered, and the filtercake was dried in vacuo; yield 0.0054 g (6.0%), mp=164–166° C.

Example 3

3-[4-(4-Phenyl-piperidin-1-yl)-benzenesulfonylamino]-propionic acid (a) 3-[4-Fluoro-(benzenesulfonylamino)]-propionic acid, sodium salt A mixture of 4-fluoro-benzenesulfonyl chloride (1.920 g, 0.009866 mol), 3-amino-propionic acid (0.980 g, 0.0110 mol), and sodium carbonate (2.33 g, 0.0220 mol) in water (15 mL) was stirred at room temperature for 28 hours, then briefly heated on a steam bath. The mixture was allowed to cool, then stirred at room temperature overnight. The mixture was reheated on a steam bath, gravity filtered hot, and allowed to cool. The filtrate was acidified to approximately pH 5 with concentrated hydrochloric acid. A white precipitate was filtered off and dried in vacuo; yield 1.907 g (78%).

$^1$H-NMR (DMSO-d$_6$): δ7.85 (m, 2H), 7.80 (br s, 1H), 7.45 (m, 2H), 2.93 (t, 2H), 2.35 (t, 2H).

(b) 3-[4-(4-Phenyl-piperidin-1-yl)-benzenesulfonylamino]-propionic acid

A stirred mixture of 3-[4-fluoro-(benzenesulfonylamino)]-propionic acid, sodium salt (0.248 g, 0.00100 mol), 4-phenyl-piperidine hydrochloride (0.218 g, 0.00110 mol), and sodium carbonate (0.317 g, 0.00299 mol) in dry dimethyl sulfoxide (3 mL) was heated in a sand bath (130° C.) under nitrogen for 22 hours. The mixture was cooled and partitioned between ethyl acetate and 1 M hydrochloric acid. The aqueous layer was extracted with additional ethyl acetate. The organics were combined, washed with saturated sodium chloride, dried (MgSO$_4$), and rotary evaporated. The residue was dissolved in dichloromethane and chromatographed on silica gel (14 g, 230–400 mesh) eluting with dichloromethane-methanol (15:1, 10×15 mL). Fractions containing product were combined, rotary evaporated and rechromatographed to give the title compound as a peach-colored solid; yield 0.082 g (21%), mp=145–147° C.

Example 4

(R)-4-Methyl-2-[4-(4-phenyl-piperidin-1-yl)-benzenesulfonylamino]-pentanoic acid

(a) (R)-2-(4-Fluoro-benzenesulfonylamino)-4-methyl-pentanoic acid

A mixture of 4-fluoro-benzenesulfonyl chloride (1.65 g, 0.00848 mol), (R)-2-amino-4-methyl-pentanoic acid (1.233 g, 0.009398 mol), and sodium carbonate (1.91 g, 0.0180 mol) in water (15 mL) was stirred at room temperature for 5 days. The solution was filtered, and the filtrate was acidified with concentrated hydrochloric acid to pH=4. The mixture was extracted with ethyl acetate. The extract was washed with saturated sodium chloride, dried (MgSO$_4$), and rotary evaporated to a yellow oil. The oil was chromatographed on silica gel (320 g, 230–400 mesh) eluting with dichloromethane-methanol (10:1, 10×300 mL). Fractions containing product were combined and rotary evaporated to give a pale yellow oil. The oil was dried in vacuo; yield 1.44 g (59%).

$^1$H-NMR (DMSO-d$_6$): δ8.1 (br s, 1H), 7.80 (m, 2H), 7.38 (m, 2H), 3.55 (t, 1H), 3.33 (br s, H$_2$O),1.56 (m, 1H), 1.36 (dd, 2H), 0.75 (dd, 6H).

(b) (R)-4-Methyl-2-[4-(4-phenyl-piperidin-1-yl)-benzenesulfonylamino]-pentanoic acid In a manner similar to Example 3(b), 4-phenyl-piperidine hydrochloride was condensed with (R)-2-(4-fluoro-benzenesulfonylamino)-4-methyl-pentanoic acid to give the title compound, mp=163–165° C.

Example 5

(S)-4-Methyl-2-[4-(4-phenyl-piperidin-1-yl)-benzenesulfonylamino]-pentanoic acid

(a) (S)-2-(4-Fluoro-benzenesulfonylamino)-4-methyl-pentanoic acid

In a manner similar to Example 4(a) (S)-2-amino-4-methyl-pentanoic acid was substituted for (R)-2-amino-4-methyl-pentanoic acid; yield 14.0 g (55%).

300 MHz $^1$H-NMR (DMSO-d$_6$): δ8.17 (br s, 1H), 7.83 (m, 2H), 7.40 (m, 2H), 3.64 (t, 1H), 1.57 (m, .1H), 1.38 (m, 2H), 0.76 (dd, 6H).

(b) (S)-4-Methyl-2-[4-(4-phenyl-piperidin-1-yl)-benzenesulfonylamino]-pentanoic acid In a manner similar to Example 3(b), 4-phenyl-piperidine hydrochloride was condensed with (S)-2-(4-fluoro-benzenesulfonylamino)-4-methyl-pentanoic acid to give the title compound, %C,H,N found: 63.96, 6.96, 6.44.

Example 6

(S)-3-Phenyl-2-[4-(4-phenyl-piperidin-1-yl)-benzenesulfonylamino]-propionic acid

(a) (S)-2-(4-Fluoro-benzenesulfonylamino)-3-phenyl-propionic acid, sodium salt In a manner similar to Example 4(a), 4-fluoro-benzenesulfonyl chloride and (S)-2-amino-3-phenyl-propionic acid were condensed to give the title compound as a white solid, mp=108–111° C.

(b) (S)-3-Phenyl-2-[4-(4-phenyl-piperidin-1-yl)-benzenesulfonylamino]-propionic acid In a manner similar to Example 3(b), (S)-2-(4-fluoro-benzenesulfonylamino)-3-phenyl-propionic acid, sodium salt and 4-phenyl-piperidine hydrochloride were condensed to give the title compound, mp=167–169° C.

Example 7

(R)-3-Phenyl-2-[4-(4-phenyl-piperidin-1-yl)-benzenesulfonylamino]-propionic acid

(a) (R)-2-(4-Fluoro-benzenesulfonylamino)-3-phenyl-propionic acid, disodium salt In a manner to Example 4(a), (R)-2-amino-3-phenyl-propionic acid was condensed with 4-fluoro-benzenesulfonyl chloride to give the title compound, mp=246–248° C.

(b) (R)-3-Phenyl-2-[4-(4-phenyl-piperidin-1-yl)-benzenesulfonylamino]-propionic acid In a manner similar to Example 3(b), (R)-2-(4-fluoro-benzenesulfonylamino)-3-phenyl-propionic acid, disodium salt was condensed with 4-phenyl-piperidine hydrochloride to give the title compound, mp=168–170° C.

Example 8

(S)-3-(1H-Indol-3-yl)-2-[4-(4-phenyl-piperidin-1-yl)-benzenesulfonylamino]-propionic acid

(a) (S)-2-(4-Fluoro-benzenesulfonylamino)-3-(1H-Indol-3-yl)-propionic acid In a manner to Example 4 (a), 4-fluoro-benzenesulfonyl chloride was condensed with (S)-2-amino-3-(1H-Indol-3-yl)-propionic acid to give the title compound, mp=57–60° C.

(b) (S)-3-(1H-Indol-3-yl)-2-[4-(4-phenyl-piperidin-1-yl)-benzenesulfonylamino]-propionic acid In a manner similar to Example 3(b), (S)-2-(4-fluoro-benzenesulfonylamino)-3-(1H-Indol-3-yl)-propionic acid was condensed with 4-phenyl-piperidine hydrochloride to give the title compound, mp=103–107° C.

Example 9

(±)-5-Phenyl-2-[4-(4-phenyl-piperidin-1-yl)-benzenesulfonylamino]-pentanoic acid

(a) (±)-2-Amino-5-phenyl-pentanoic acid

A stirred suspension of (±)-2-(acetylamino)-5-phenyl-pentanoic acid (0.5003 g, 0.002126 mol) in 2.8 M hydrochloric acid was refluxed for 2 hours, and the resulting brown solution was allowed to cool. A tan precipitate formed upon cooling. The solids were filtered off, and the filtrate was rotary evaporated to give a yellow gum. The gum was dissolved in hot water, gravity filtered, and allowed to cool. The mixture was made basic with 1 M sodium hydroxide to pH=5. The resulting precipitate was filtered off, washed with water, and dried in vacuo to give a yellow solid; yield 0.205 g (50%), mp=213–215° C.

(b) (±)-2-(4-Fluoro-benzenesulfonylamino)-5-phenyl-pentanoic acid

A mixture of (±)-2-amino-5-phenyl-pentanoic acid (0.188 g, 0.000973 mol), 4-fluoro-benzenesulfonyl chloride (0.189 g, 0.000971 mol), and sodium carbonate (0.208 g, 0.00196 mol) in water (4 mL) was stirred at room temperature for 4 days. The mixture was heated briefly on a steam bath to give a cloudy solution. The solution was gravity filtered hot, and the filtrate allowed to cool. The resulting solid that crystallized was filtered off, washed with water, and dried in vacuo; yield 0.131 g, (38%). $^1$H-NMR (DMSO-$d_6$): δ7.81 (m, 2H), 7.37 (t, 2H), 7.25 (t, 2H), 7.14 (m, 4H), 3.34 (br s, $H_2$), 3.04 (t, 1H), 2.46 (m, 2H), 1.6–1.4 (m, 4H).

(c) (±)-5-Phenyl-2-[4-(4-phenyl-piperidin-1-yl)-benzenesulfonylamino]-pentanoic acid In a manner similar to Example 3(b), (±)-2-(4-fluoro-benzenesulfonylamino)-5-phenyl-pentanoic acid was condensed with 4-phenyl-piperidine hydrochloride to give the title compound, mp=59–62° C.

Example 10

[4-(4-Phenyl-piperazin-1-yl)-benzenesulfonylamino]-acetic acid

In a manner similar to Example 3(b), (4-fluoro-benzenesulfonylamino)-acetic acid was condensed with 4-phenyl-piperazine to give the title compound, mp=120–124° C.

Example 11

{Isobutyl-[4-(4-phenyl-piperidin-1-yl)-benzenesulfonyl]amino}-acetic acid (a) Isobutylamino-acetic acid, ethyl ester hydrochloride A mixture of isobutylamine (0.90 mL, 0.0091 mol), bromoacetic acid, ethyl ester (1.0 mL, 0.0090 mol), and triethylamine (1.28 mL, 0.00918 mol) in diethylether (15 mL) was stirred at room temperature for 24 hours. The resulting suspension was filtered off and washed with diethylether. The filtrate and washings were combined and rotary evaporated to an oil. The oil was chromatographed on silica gel (150 g, 230–400 mesh) eluting with dichloromethane-diethylether (19:1, 8×125 mL; 15:1, 7×125 mL; 10:1, 15×125 mL). Fractions containing product were combined and rotary evaporated to give an oil. The oil was dissolved in diethylether, concentrated hydrochloric acid (0.52 mL, 0.0063 mol HCl) was added, and the volatiles were rotary evaporated to give a white solid. The solid was dried in vacuo; yield 1.0 g (59%).

$^1$H-NMR (DMSO-$d_6$): δ9.23 (br s, 2H), 4.22 (q, 2H), 3.96 (m, 2H), 3.41 (br s, $H_2O$), 2.78 (m, 2H), 2.00 (m, 1H), 1.25 (t, 3H), 0.94 (d, 6H).

(b) [(4-Fluoro-benzenesulfonyl)-isobutyl-amino]-acetic acid

A mixture of isobutylamino-acetic acid, ethyl ester hydrochloride (0.359 g, 0.00183 mol) in. 6 M hydrochloric acid (10 mL) was refluxed for 20 hours and allowed to cool. The mixture was made basic with 50% wt/wt sodium hydroxide and 1 M sodium hydroxide to pH=5, and the volatiles were rotary evaporated. The residue was triturated 3 times with boiling methanol, and the triturates were combined and rotary evaporated. The residue was triturated 3 times with hot acetic acid, and the triturates were combined and rotary evaporated. The residue was dissolved in water and freeze-dried to give a white solid. This solid was combined with 4-fluoro-benzenesulfonyl chloride (0.3334 g, 0.001713 mol) and sodium carbonate (0.547 g, 0.00516 mol) in water, and the mixture was stirred at room temperature for 3 days. The mixture was acidified with concentrated hydrochloric acid and extracted with ethyl acetate. The extract was dried (MgSO$_4$) and rotary evaporated to a white solid. The solid was chromatographed on silica gel (15 g, 230–400 mesh) eluting with dichloromethane-methanol (10:1, 10×15 mL). Fractions containing product were combined and rotary evaporated to give a white solid. The solid was dried in vacuo; yield 0.32 g (64% overall).

$^1$H-NMR (DMSO-$d_6$): δ7.85 (m, 2H), 7.39 (m, 2H), 3.91 (s, 2H), 3.32 (br s, $H_2O$), 2.94 (d, 2H), 1.77 (m, 1H), 0.79 (d, 6H).

(c) {Isobutyl-[4-(4-phenyl-piperidin-1-yl)-benzenesulfonyl]amino}-acetic acid

In a manner similar to Example 3(b), [(4-fluoro-benzenesulfonyl)-isobutyl-amino]-acetic acid was condensed with 4-phenyl-piperidine hydrochloride to give the title compound, mp=140–143° C.

Example 12

(S)-2-[4-(4-Benzyl-piperidin-1-yl)-benzenesulfonylamino]-3-phenyl-propionic acid In a manner similar to Example 3(b), (S)-2-(4-fluoro-benzenesulfonylamino)-3-phenyl-propionic acid, sodium salt, and 4-benzyl-piperidine were condensed to give the title compound, mp=164–165° C.

Example 13

(S)-3-(4-Benzyloxy-phenyl)-2-[4-(4-phenyl-piperidin-1-yl)-benzenesulfonylamino]-propionic acid (a) (S)-3-(4-Benzyloxy-phenyl)-2-(4-fluoro-benzenesulfonylamino)-propionic acid A mixture of (S)-2-amino-3-(4-benzyloxy-phenyl)-propionic acid (2.7 g, 0.010 mol), 4-fluoro-benzenesulfonyl chloride (2.0 g, 0.010 mol), and sodium carbonate (2.2 g, 0.020 mol) in a mixture of tetrahydrofuran (20 mL) and water (20 mL) was stirred at room temperature for 3 days. The reaction mixture was partitioned between ethyl acetate and 1 M hydrochloric acid. The organic layer was washed with saturated sodium chloride solution, dried (MgSO$_4$), and rotary-evaporated under reduced pressure to give an oil. The oil was chromatographed on silica gel (445 g, 230–400 mesh) eluting with dichloromethane-methanol (20:1), and the fractions containing product were rotary-evaporated to give a solid. The solid was recrystallized from toluene to give the title compound as a light yellow solid; yield 0.22 g (5%), mp=138–139° C.

(b) (S)-3-(4-Benzyloxy-phenyl)-2-[4-(4-phenyl-piperidin-1-yl)-benzenesulfonylamino]-propionic acid In a manner similar to Example 3(b), (S)-3-(4-benzyloxy-phenyl)-2-(4-fluoro-benzenesulfonylamino)-propionic acid was condensed with 4-phenyl-piperidine hydrochloride to give the title compound, mp=75–78° C.

Example 14

(S)-3-(4-Hydroxy-phenyl)-2-[4-(4-phenyl-piperidin-1-yl)-benzenesulfonylamino]-propionic acid To a room temperature, stirred mixture of (S)-3-(4-benzyloxy-phenyl)-2-[4-(4-phenyl-piperidin-1-yl)-benzenesulfonylamino]-propionic acid (0.033 g, 0.000058 mol) in thioanisole (0.34 mL) was added trifluoroacetic acid (1 mL), and the mixture was stirred for 18 hours. The reaction mixture was poured into water and extracted with ethyl acetate. The organic layer was dried ($Na_2SO_4$) and rotary-evaporated under reduced pressure to remove volatiles. The resulting yellow solution was chromatographed on silica gel (5.5 g) eluting with dichloromethane (10×5 mL) followed by dichloromethane-methanol (14:1). Fractions containing product were rotary-evaporated. The residue was suspended in water and stirred to give the title compound as an off-white solid; yield 0.0079 g (28%), mp 108–110° C.

Example 15

(S)-3-Phenyl-2-[4-(4-phenyl-piperazin-1-yl)-benzenesulfonylamino]-propionic acid In a manner similar to Example 3(b), (S)-2-(4-fluoro-benzenesulfonylamino)-propionic acid, sodium salt and 4-phenyl-piperazine were condensed to give the title compound as a beige solid, mp=192–193° C.

Example 16

(S)-2-{4-[-4-(3-Methoxy-phenyl)-piperazin-1-yl]-benzenesulfonylamino}-3-phenyl-propionic acid In a manner similar to Example 3(b), (S)-2-(4-fluoro-benzenesulfonylamino)-propionic acid, sodium salt and 4-(3-methoxy-phenyl)-piperazine were condensed to give the title compound as a pale red-brown solid, mp=137–139° C.

Example 17

(S)-2-{4-[-4-(3-Hydroxy-phenyl)-piperazin-1-yl]-benzenesulfonylamino}-3-phenyl-propionic acid hydrobromide To a stirred suspension of (S)-2-{4-[4-(3-methoxy-phenyl)-piperazin-1-yl]-benzenesulfonylamino}-3-phenyl-propionic acid (0.103 g, 0.000208 mol) in dichloromethane (2 mL) at −78° C. under nitrogen was added dropwise a 1.0 M solution of boron tribromide in dichloromethane (1.0 mL, 0.0010 mol). The mixture was stirred for 15 minutes at −78° C. and then allowed to warm to +3° C. After 6 hours, the reaction mixture was diluted with water. The resulting suspension was stirred overnight. The solids were filtered off, washed with additional water, and dried in vacuo to give the title compound as an off-white solid; yield 0.069 g (69%), mp=229–230° C.

Example 18

(S)-2-{4-[-4-(4-Methoxy-phenyl)-piperazin-1-yl]-benzenesulfonylamino}-3-phenyl-propionic acid In a manner similar to Example 3(b), (S)-2-(4-fluoro-benzenesulfonylamino)-propionic acid, sodium salt and 4-(4-methoxy-phenyl)-piperazine dihydrochloride were condensed to give the title compound as a brown solid, mp=203–205° C.

INHIBITION STUDIES

Experiments were carried out which demonstrate the efficacy of compounds of Formula I as potent inhibitors of stromelysin-1 and gelatinase A. Experiments were carried out with the catalytic domains. Table 1 shows the activity of the Examples 1–12 versus GCD (recombinant gelatinase A catalytic domain); SCD (stromelysin-1 catalytic domain). $IC_{50}$ values were determined using a thiopeptolide substrate, Ac-Pro-Leu-Gly-thioester-Leu-Leu-Gly-OEt (Ye Q.-Z., Johnson L. L., Hupe D. J. and Baragi V., "Purification and Characterization of the Human Stromelysin Catalytic Domain Expressed in *Escherichia coli*", *Biochemistry*, 1992;31:11231–11235).

TABLE 1

| Compound Number | $IC_{50}$ μM/SCD | $IC_{50}$ μM/GCD |
|---|---|---|
| 1 | 0.02 | 0.21 |
| 2 | 0.019 | 0.81 |
| 3 | 1.24 | 4.8 |
| 4 | 0.036 | 0.93 |
| 5 | 0.011 | 0.084 |
| 6 | 0.014 | 0.22 |
| 7 | 0.012 | 0.12 |
| 8 | 0.01 | 0.32 |
| 9 | 0.30 | 0.40 |
| 10 | 0.05 | 0.50 |
| 11 | 0.17 | 3.3 |
| 12 | 0.60 | 3.2 |
| 13 | 0.19 | 5.3 |
| 14 | 0.015 | 0.13 |
| 15 | 0.021 | 0.088 |
| 16 | 0.062 | 0.33 |
| 17 | 0.077 | 0.18 |
| 18 | 0.014 | 0.033 |

What is claimed is:

1. A method of inhibiting a matrix metalloproteinase, the method comprising administering to a patient in need of matrix metalloproteinase inhibition a matrix metalloproteinase inhibiting amount of a compound of Formula I

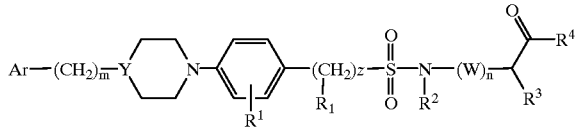

wherein:
Ar is selected from phenyl;
  phenyl substituted with alkyl, —$NO_2$, halogen, —$OR^5$, —CN, —$CO_2R^5$, —$SO_3R^5$, —CHO, —$COR^5$, —$CONHR^5$, —$NHR^5$, or —$NHCOR^5$;
  heteroaryl; or
  2-naphthyl;
$R^1$ is hydrogen, methyl, —$NO_2$, —Cl, —$NH_2$, —$NHCO_2CH_3$, —OH, or —$CO_2H$;
$R^2$ and $R^3$ are the same or different and are independently selected from hydrogen, alkyl, —$(CH_2)_v$-aryl, —$(CH_2)_v$-heteroaryl, —$(CH_2)_v$-cycloalkyl, —$(CH_2)_p$—X—$(CH_2)_q$-aryl, —$(CH_2)_p$—X—$(CH_2)_q$-heteroaryl, —$(CH_2)_t$—$NR^6R^{6a}$, —$(CH_2)_v$—$R^7$, —$(CH_2)_v$—$CO_2R^5$, —$(CH_2)_v$—$CONR^6R^{6a}$, or —$(CH_2)_v$—$SR^5$;
m is zero or 1;

Y is CH;
z is zero or 1;
W is —CHR$^8$;
n is zero or 1;
R$^4$ is —OH, —NR$^6$R$^{6a}$, or —NHOR$^9$;
R$^5$ is hydrogen or alkyl;
v is 1 to 5;
X is O or S;
p and q are independently 1 to 5, provided that p+q is not greater than 5;
t is 1 to 9;
R$^6$ and R$^{6a}$ are each the same or different and are hydrogen or alkyl;
R$^7$ is 1,3-dihydro-1,3-dioxo-2H-isoindol-2-yl, or 1,3-dihydro-1,3-dioxo-benzo[f]isoindol-2-yl;
R$^8$ is hydrogen or alkyl;
R$^9$ is hydrogen, alkyl, or benzyl; or
a pharmaceutically acceptable salt thereof.

2. The method of claim 1 wherein the matrix metalloproteinase is stromelysin-1.

3. The method of claim 1 wherein the matrix metalloproteinase is gelatinase-A.

4. The method of claim 1, wherein the patient in need of matrix metalloproteinase inhibition is suffering from an atherosclerotic plaque.

5. The method of claim 1, wherein the patient in need of matrix metalloproteinase inhibition has an aortic aneurism.

6. The method of claim 1, wherein the compound of formula I is administered to the patient to prevent restenosis following balloon angioplasty, graft or shunt implantation, or atherectomy.

7. The method of claim 1, wherein the patient in need of matrix metalloproteinase inhibition is suffering from periodontal disease.

8. The method of claim 1, wherein the patient in need of matrix metalloproteinase inhibition is suffering from burns.

9. The method of claim 1, wherein the patient in need of matrix metalloproteinase inhibition is suffering from decubital ulcers.

10. The method of claim 1, wherein the patient in need of matrix metalloproteinase inhibition is suffering from chronic ulcers or wounds.

11. The method of claim 1, wherein the compound of formula I is administered to the patient to prevent tumor angiogenesis and tumor cell invasion.

12. The method of claim 1, wherein the patient in need of matrix metalloproteinase inhibition is suffering from arthritis.

13. The method of claim 1, wherein the patient in need of matrix metalloproteinase inhibition is suffering from an autoimmnune or inflammatory disorder dependent upon tissue invasion by leukocytes.

14. The method of claim 1, wherein the compound of formula I is administered as a pharmaceutical composition comprising the compound of formula I and a pharmaceutically acceptable carrier.

15. The method of claim 1, wherein the patient in need of matrix metalloproteinase inhibition is suffering from multiple sclerosis.

* * * * *